(12) United States Patent
Salcudean et al.

(10) Patent No.: US 6,425,865 B1
(45) Date of Patent: Jul. 30, 2002

(54) ROBOTICALLY ASSISTED MEDICAL ULTRASOUND

(75) Inventors: Septimiu E. Salcudean, Vancouver; Graham S. Bell, Niagara-on-the Lake; Peter D. Lawrence, Vancouver; Alexei Marko, Vancouver; Michael Jameson, Vancouver, all of (CA)

(73) Assignee: The University of British Columbia, Vancouver (CA)

(*) Notice: Subject to any disclaimer, the term of this patent is extended or adjusted under 35 U.S.C. 154(b) by 0 days.

(21) Appl. No.: 09/330,598

(22) Filed: Jun. 11, 1999

Related U.S. Application Data

(60) Provisional application No. 60/089,170, filed on Jun. 12, 1998.

(51) Int. Cl.[7] .............................................. A61B 08/00
(52) U.S. Cl. ...................................... 600/437; 600/111
(58) Field of Search ................................. 600/439, 437, 600/111, 438; 378/117; 606/1

(56) References Cited

U.S. PATENT DOCUMENTS

| 5,654,997 A | * | 8/1997 | Brownell et al. ............ 378/117 |
| 5,749,362 A | * | 5/1998 | Funda et al. ................. 600/111 |
| 5,820,623 A | * | 10/1998 | Ng ................................. 606/1 |
| 6,086,535 A | * | 7/2000 | Ishibashi et al. ............ 600/439 |

* cited by examiner

Primary Examiner—Marvin M. Lateef
Assistant Examiner—Maulin Patel
(74) Attorney, Agent, or Firm—Oyen Wiggs Green & Mutala

(57) ABSTRACT

A system for medical ultrasound in which the ultrasound probe is positioned by a robot arm under the shared control of the ultrasound operator and the computer is proposed. The system comprises a robot arm design suitable for diagnostic ultrasound, a passive or active hand-controller, and a computer system to co-ordinate the motion and forces of the robot and hand-controller as a function of operator input, sensed parameters and ultrasound images.

43 Claims, 4 Drawing Sheets

ROBOTICALLY ASSISTED MEDICAL ULTRASOUND

This application claims Convention priority on U.S. provisional patent application Ser. No. 60/089,170, filed Jun. 12, 1998.

TECHNICAL FIELD

The present invention relates to a method and apparatus to perform ultrasound image acquisition for diagnostic or intervention using a robot to position the ultrasound transducer.

BACKGROUND

Ultrasound as a medical imaging modality has a number of benefits—it is inexpensive, non-invasive, real-time, etc. It is used widely for diagnosis, and also in interventions, for example, to guide needles or other instruments for anaesthesis and surgery.

Medical ultrasound examinations often require that ultrasound technicians hold the transducer probe in one hand while adjusting scanning parameters with the other hand, or hold the transducer in awkward positions for prolonged periods of time, sometimes exerting large forces for prolonged periods of time. Not surprisingly, a number of studies indicate that the technicians suffer from an unusually high incidence of musculoskeletal disorders (e.g. Vanderpool, 1993, Craig, 1985).

The use of a robot in conjunction with ultrasound imaging has been described in U.S. Pat. No. 5,817,022, Vesely et al., that discloses a system that enables the display of 2-D ultrasound images in a 3-D viewing environment. The use of a robot to position a surgical/medical intervention instrument under computer control is discussed as an option, but the ultrasound transducers described in that method are fixed. The role of the operator, position or force sensors of ultrasound image in the positioning of the instrument is not discussed.

A robot-assisted ultrasound examination system would provide other, not only ergonomic, benefits. For instance, since the location of the ultrasound transducer can be determined via the forward kinematics of the slave manipulator, three-dimensional ultrasound images can be reconstructed from a series of two-dimensional image slices. The process of creating three-dimensional ultrasound images from a series of two-dimensional slices has been suggested in Iezzi et al., U.S. Pat. No. 5,551,432, which teaches a three-dimensional ultrasound imaging system that employs a motor with a screw drive to translate the ultrasound transducer in order to achieve images of the eye. U.S. Pat. No. 5,551,432 also describes an Auto-scroll feature that enables the operator to command the speed at which the transducer is translated. U.S. Pat. No. 5,810,008, Dekel et al., describes a three-dimensional ultrasound imaging system comprising position and orientation sensors that enable multiple planar computer images to be correlated to form three-dimensional ultrasound images. Another three-dimensional ultrasound imaging system that uses an actuator to move the ultrasound transducer is described in U.S. Pat. No. 5,759,153, Webler et al. Yet another three-dimensional ultrasound imaging system is described in U.S. Pat. No. 5,842,473, Fenster et al.

Remote probe positioning could also be used in teleradiology to examine patients at distant or inaccessible locations. Although a number of methods for transmitting ultrasound images have been proposed in the literature (Sublett, 1995), none allow the radiologist to view and manipulate the ultrasound transducer at the remote site. The remote positioning of an ultrasound transducer for endoscopic applications has been described in a number of patents. U.S. Pat. No. 5,842,993, Eichelberger et al., describes a navigable ultrasonic imaging probe assembly that can be positioned by the user endoscopically. Another endoscopic ultrasound transducer positioning system is described in European Patent application No. 0 514 584 A2, Solomon et al.

The computer-controlled positioning of an ultrasound probe has been described in other applications. For example, U.S. Pat. No. 5,836,880, Pratt, describes an animal tissue scanning system comprising a computer-positioned ultrasound transducer. However, such positioning has not been done as a function of sensed variables, such as ultrasound transducer position, forces or the image it acquires.

The control of multiple parameters for ultrasound image acquisition can be quite difficult. A control architecture suitable for controlling an ultrasound imager or other complex equipment is described in U.S. Pat. No. 5,853,367. The system is concerned with the efficient distribution of task loading for complex computerized systems.

The ability to position the ultrasound transducer in response to acquired ultrasound images would also be of benefit to image-guided interventions (e.g., percutaneous pericardial puncture) and registration with past examination records or images obtained with other imaging methods (e.g., MRI). The use of ultrasound imaging together with three-dimensional tracking of the transducer probe has been proposed in U.S. Pat. No. 5,797,849 as a tool for improving medical interventions.

SUMMARY OF INVENTION

A system for medical ultrasound is presented in which the ultrasound probe is positioned by a robot arm under the shared control of the ultrasound operator and the computer. The system comprises a robot arm design suitable for diagnostic ultrasound, a passive or active hand-controller, and at least one computer system to coordinate the motion and forces of the robot and hand-controller as a function of operator input, sensed parameters and ultrasound images.

While the ultrasound probe is positioned by a robot, the operator, the robot controller, and an ultrasound image processor have shared control over its motion. The motion of the robot arm and the hand controller of the proposed ultrasound are based on measured positions and forces, acquired ultrasound images, and/or taught position and force trajectories. Several modes of control are presented, including the control of the transducer using ultrasound image tracking.

An inherently safe, light, backdrivable, counterbalanced robot has been designed for carotid artery examinations but can be easily adapted for other examinations.

To operate the system, the ultrasound technician manipulates a hand-controller and enters commands via a user interface. The hand controller displacement and/or forces are sensed by appropriate sensors and read in by a computer that interprets these as a desired ultrasound transducer location or velocity or force or combination thereof (by location we mean position and orientation). A suitably designed mechanism, preferably a backdriveable, counterbalanced and light robot, positions the ultrasound transducer against the human body according to the above desired and possibly scaled values. The ultrasound transducer image is displayed on a monitor observed by the ultrasound technician, who can alter the ultrasound transducer location and force by manipulating the hand controller or entering commands via the operator interface. The operator can either control all degrees of freedom of the ultrasound transducer by manipulating the hand controller, or can control fewer degrees of freedom, with the remaining degrees of freedom being controlled by a computer. The computer-controlled degrees of freedom could specify a particular location or velocity trajectory, such as a probe translation or rotation motion, or a particular force, or the tracking of a particular feature in the ultrasound image acquired by the ultrasound machine, or a previously executed trajectory. To give the operator an intuitive way of controlling the forces the ultrasound transducer exerts on the human body, the hand controller could be active, i.e. have actuators that can exert a force on the ultrasound technician's hand. These forces could be proportional to the ultrasound transducer forces.

The invention is directed to a method of positioning an ultrasound transducer onto the surface of a human body comprising: mechanically positioning the ultrasound transducer on the surface of the human body by an operator positioned remotely from the ultrasound transducer operating a hand controller which is linked to the ultrasound transducer and which by means of a programmed computer instructs and causes the ultrasound transducer to be positioned on the surface of the human body, the ultrasound transducer then acquiring and transmitting ultrasound images electronically to a display viewed by the operator.

The hand controller can control electronically and remotely the position of the ultrasound transducer on the human body, the velocity of the ultrasound transducer over the human body or the force exerted by the ultrasound transducer on the human body. The hand controller can control electronically and remotely the velocity and force of the ultrasound transducer on the human body. The hand controller can control only some of the degrees of freedom available to the ultrasound transducer.

The computer can be programmed to hold the ultrasound transducer at a fixed position on the human body, and the operator can be permitted to control orientation of the ultrasound transducer. The degree of force exerted by the transducer can be controlled by the computer according to a force sensor reading and the operator can be permitted to control orientation of the ultrasound transducer.

When normal force exerted by the transducer is controlled by the computer, the pitch of the ultrasound transducer can be adjusted to a stated program value in the computer. The hand controller can be a joy stick which can provide force and feedback to the operator.

The connection between the positioning of the ultrasound transducer and the operator and the hand controller can be performed by means of a counterbalanced robot. The program in the computer can control certain degrees of freedom and the counterbalanced robot can control other degrees of freedom.

The invention is also directed to a method of performing ultrasound on a person comprising using a robot arm to position an ultrasound probe on the surface of the person according to shared control of a remotely positioned ultrasound operator and a programmed computer, the ultrasound probe acquiring and transmitting ultrasound images to a display viewed by the operator.

The ultrasound transducer probe information can be displayed on the monitor, and the operator can activate the hand controller to regulate the force applied by the ultrasound transducer probe on the surface of the human body. The operator can control motion of the ultrasound transducer probe along certain degrees of freedom and the programmed computer can control the motion of the ultrasound transducer probe along other degrees of freedom.

The computer can be programmed to recall trajectories followed by the ultrasound transducer probe during a prior ultrasound scan of the human body. The computer can be programmed to recall serial positions and serial forces applied by the ultrasound transducer probe during a prior serial position and serial force trajectory followed by the ultrasound transducer probe on the human body.

The computer can be programmed to repeat scans of the ultrasound transducer probe from different incremental positions on the human body lateral to the scan direction and rationalize the repeated scans to generate a three-dimensional ultrasound image on the monitor.

The computer can be programmed to perform mixed modes of operation wherein the operator shares control of the position of the ultrasound transducer probe along certain axes with taught control programmed into the computer and a tracking mode along a plane is programmed in the computer while the operator controls the movement of the ultrasound transducer probe along the remaining degrees of freedom. Control of the position, force or velocity of the ultrasound transducer can be shared between the operator and the computer and determined according to the ultrasound image.

The operator can use an input device to input a component of motion control to the transducer to scan new parts of the human body and to input a component of orientation control to the transducer while observing the ultrasound images generated by the ultrasound image monitor to maximize image signal-to-noise ratio.

Ultrasound image features can be processed by the computer to determine the optimum orientation of the transducer and provide an automatic orientation control signal component which can be added to the attitude control input from the operator's input device.

The transducer image features can be processed by the computer to provide an automatic direction control signal component which can track relevant anatomical structures under the surface of the skin of the human body.

The computer can sense the force vector applied by the operator to the input device and can scale the force up or down and add it to a predetermined force applied between the transducer and the human body. The input device can be capable of displaying a force vector to the operator that can be computed by the computer based scaling the actual force observed at the probe/skin interface of the human body.

The direction of motion of the transducer can be determined from a recording of a previous scan. The hand controller can be a joy stick which can provide force feedback to the operator.

The invention is also directed to an apparatus for positioning an ultrasound transducer onto a human body comprising: (a) a mechanism to position the ultrasound transducer on the human body; (b) a hand controller to enable an operator to input into a computer a desired position, a desired velocity or a desired force, or a linear combination thereof; (c) a computer control that maps the operator input into the ultrasound transducer position, velocity or force.

The hand controller can control the position of the transducer, the velocity of the transducer, the force of the transducer, or a linear combination of velocity and force of the transducer.

The hand controller can be a 6 degrees of freedom joy stick which can provide force-feedback to an operator of the apparatus. The joy stick might control only some of the degrees of freedom of the transducer.

The mechanism can be a counterbalanced robot. The robot can have a 4-bar linkage wrist. The apparatus can include a 6 degrees of freedom rate control device.

The invention is also directed to an apparatus for performing ultrasound on a person comprising: (a) a robot arm with an ultrasound transducer for positioning the transducer on the surface of the body of the person; (b) a passive or active hand controller which is operated by an operator to instruct the robot arm to position the ultrasound transducer on the surface of the body of the person; and (c) a computer which is programmed to coordinate motion and force of the robot and hand controller as a function of operator input, sensed parameters and ultrasound images.

The operator can control the apparatus in a master-slave mode, and the robot can track operator position, velocity or force. The hand controller can be passive or active.

BRIEF DESCRIPTION OF DRAWINGS

In drawings which illustrate specific embodiments of the invention, but which should not be construed as restricting the spirit or scope of the invention in any way.

DESCRIPTION OF THE INVENTION

Figure 1:
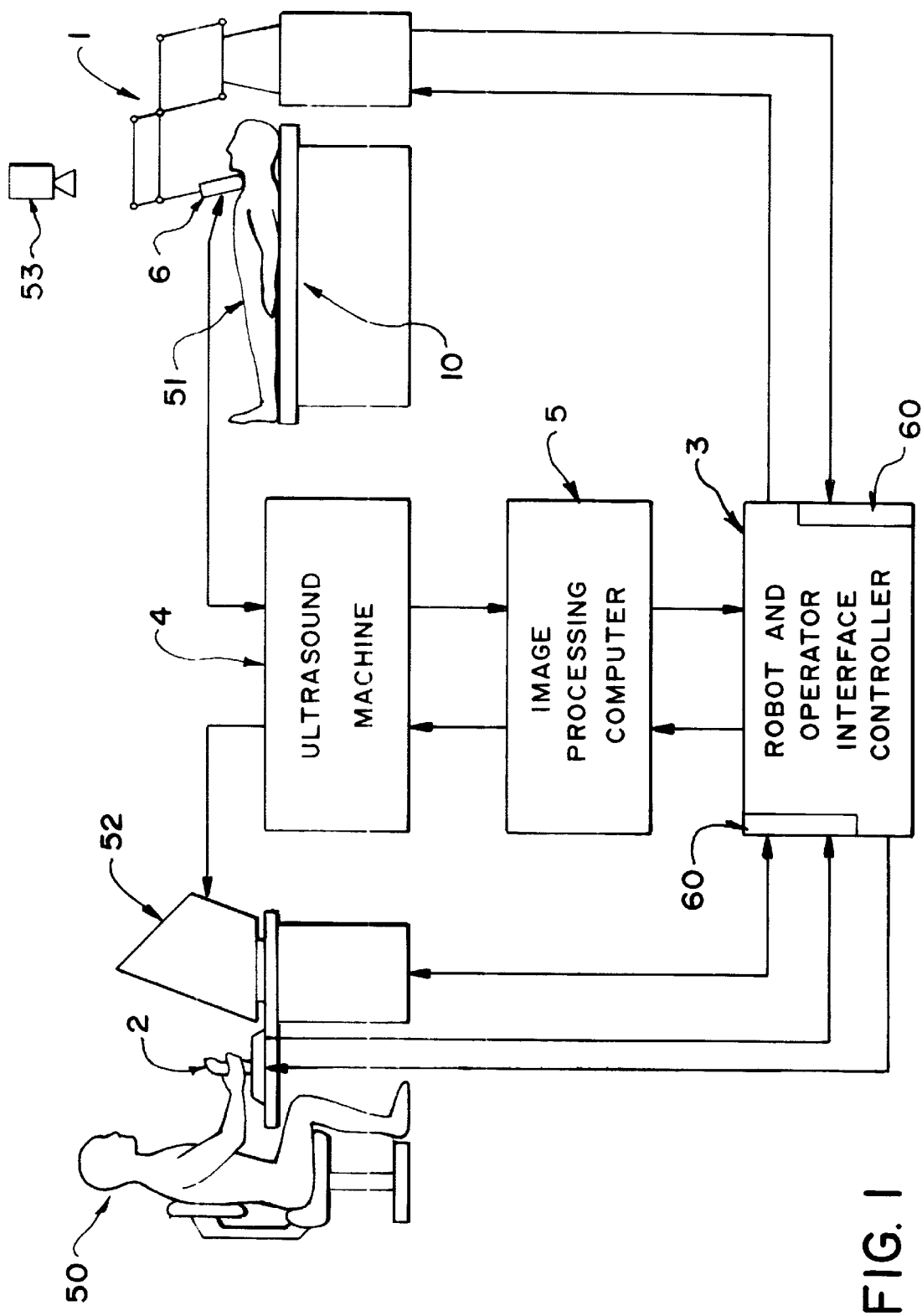
FIG. 1 illustrates a schematic of the robotically assisted medical ultrasound, including operator, monitor, ultrasound diagnosis machine, robot controller, counterbalanced arm and ultrasound probe.

Motivated initially by the need to alleviate the problems encountered by ultrasound technicians and present a more ergonomic interface to the ultrasound technician, the present invention proposes a teleoperation system to be used for medical ultrasound examinations. The system consists of a master hand controller, a slave manipulator carrying the ultrasound probe, and associated computer systems that allow the operator to remotely position the ultrasound transducer relative to the patient's body. One of the problems considered was carotid artery examination, which is carried out to detect occlusive disease in the left and right common carotid arteries a major cause of strokes.

The proposed ultrasound system consists of a special-purpose robot arm carrying the ultrasound probe, a passive or active hand-controller to be used by the operator, and a real-time computer that controls the motion of the robot arm and the hand controller based on measured positions and or velocities and forces, acquired ultrasound images, and/or taught position and force trajectories.

The feasibility of the invention has been tested for carotid artery examination. Based on force and position measurements, the kinematic structure of a robot has been designed and the robot parameters are now being optimized. Ultrasound images are available for "visual servoing". Although visual servoing has been demonstrated for conventional camera-based images, only limited feasibility of tracking or zero-ing on ultrasound images has been demonstrated to date using correlation techniques in spatial and frequency domain.

Several modes of operation are envisaged:
Operator Control.

The operator controls the system in master-slave mode, with the robot tracking operator positions, velocity or force commands. The hand controller may be passive or active. With an active hand controller, ultrasound probe force information can be displayed directly to the operator hand, allowing a more direct and intuitive control of ultrasound probe forces.

Shared Control.

The operator controls the motion of the ultrasound probe along some degrees of freedom (for example, positions along directions tangent to the body), while the computer controls the motion along other degrees of freedom (for example, force along the normal to the body).

Taught Control.

The computer can remember trajectories (positions and forces), allowing effortless repeat scans in the same mode.

Ultrasound Image Tracking Mode.

The computer can be programmed in instances in which ultrasound image features need to be recognized and tracked (e.g., when a vessel such as the carotid artery needs to be scanned longitudinally, or when the motion of a needle has to be tracked).

3-D Reconstruction Mode.

In such a mode, the computer controlling the robot would optimize the scanning type to improve the acquisition of 3-D ultrasound images.

Mixed Modes.

The above modes of operation can be mixed, for example, some shared control along some axis with taught control in others, tracking mode in a plane with operator control along the axis orthogonal to it. In addition, ultrasound images and the ultrasound robot internal position sensors may be used to register the patient to an absolute coordinate.

An overview of the hardware of the ultrasound system is shown in FIG. 1 and consists of a special-purpose robot arm 1 carrying the ultrasound probe 6 from the ultrasound machine 4, a passive or active hand-controller 2 to be used by the operator, and a controller 3 that controls the motion of the robot arm 1 and the hand controller 2. An image processing computer 5 can be used to process the ultrasound images acquired by the ultrasound machine. It is understood that if the object of using the present robot-assisted ultrasound system is to perform medical ultrasound examinations at a significant distance, some means of displaying the position of the ultrasound transducer is required. This could be accomplished by a camera 53 mounted so the patient 51 is in its field of view and transmitting the images into a window of the display 52 used by the system operator 50.

Ultrasound Positioning Robot 1

The invention feasibility has been examined for carotid artery examination. Measurements of the ultrasound probe motion and exerted forces during carotid artery examinations have been taken. Possible robot structures have been evaluated based on these measurements and other requirements, such as low mass and counterbalanced design that are needed in a hospital environment. It was determined by the inventors that an ultrasound probe-positioning robot having a parallelogram linkage wrist would be suitable because of its large motion range and remote center of rotation of the probe.

Figure 2:
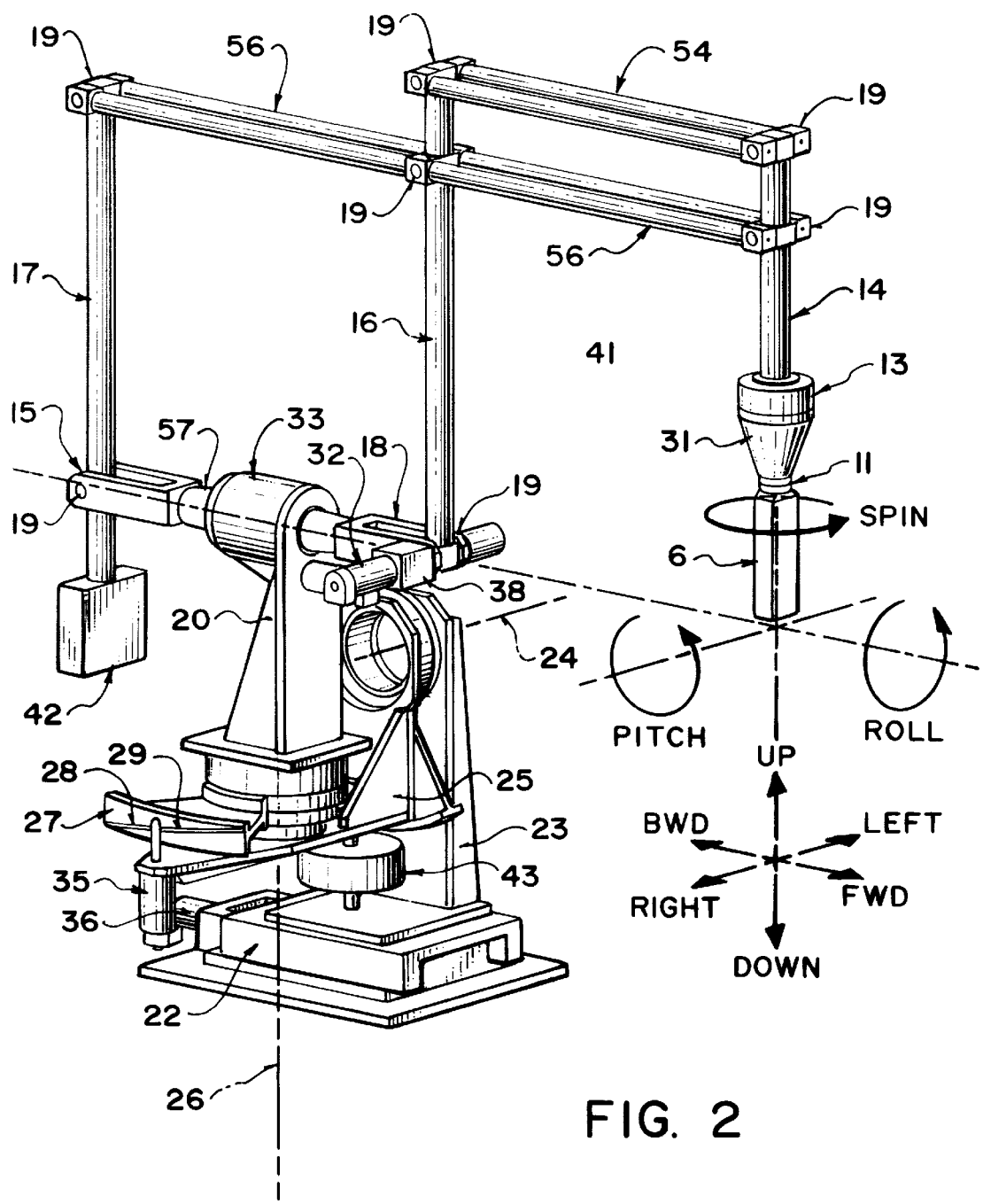
FIG. 2 illustrates an isometric view of the counterbalanced robotic arm and ultrasound probe mounted on it.

The proposed ultrasound probe carrying robot is described in detail in FIG. 2. The ultrasound probe 6 is mounted on a magnetic holder 11, which is mounted in turn on the shaft of a probe yawing motor and encoder 31 that can change the ultrasound probe SPIN angle. The magnetic holder is designed so the probe hold is broken away for large forces in order to have a mechanical safety system that prevents the ultrasound probe 6 from hurting the patient 51. The motor is mounted on a force-torque sensor 13 that is in turn mounted on a support arm 14. The wrist linkage is designed to form a planar parallelogram linkage that keeps links 14, 16 and 17 parallel to each other, and links 54, 56 and 57 parallel to each other. Link 57 is the base link of the parallelogram structure and consists of the motor assembly 33 and the two forks 15 and 18. Links 14, 16, 17 and 54, 56 and 57 are held in a planar parallelogram structure by parallel axis joints 19. Motor and encoder 32 is attached to a transmission 38 mounted on the fork 18 and can change the probe PITCH angle by changing the angle between link 16 (and hence links 14 and 17) and link 57 (and hence links 54 and 56). Motor and encoder with transmission 33 can rotate the entire parallel linkage changing the ultrasound probe ROLL angle.

The parallelogram wrist described in this invention keeps the center of the ultrasound probe 6 at a fixed point when the base of the wrist 20 is fixed. This is advantageous for medical ultrasound examinations as the probe is often held by the sonographer at a given tip position and oriented about its tip to acquire images of interest. The orientation motion of the wrist is given by manoeuvring only three motors—the wrist motors 31, 32 and 33. The force-torque sensor 13 measures the reaction torque due to turning of motor 31 and the direct forces and torques that are applied on the ultrasound probe in directions other than the SPIN direction. The counterweight 41 ensures that the parallelogram wrist linkage center of mass lies at a fixed point on its roll axis, causing the parallelogram linkage wrist loading onto its support structure 20 to be equivalent to a mass point, regardless of its orientation.

The ultrasound probe carrying robot parallogram linkage wrist attaches to the supporting structure 20 of a three-axis arm, consisting of a translation table 22 actuated by a lead-screw driven by a motor 36. Motion of the translation table 22 moves the ultrasound probe in the forward (FWD) and backward (BWD) directions. Two rotational links are mounted serially on the translation table 22. The first one is attached to the translation table 22 by a bracket 23, and has a horizontal rotation axis 24 that tilts the platform 25 and causes the ultrasound probe 6 to move essentially up and down.

The second one is attached to the platform 25 and rotates about a vertical axis 26 and causes the ultrasound probe to pan essentially left and right.

The pan motor 35 pans the structure via a capstan mechanism having a drum 27 on which two wires 28 and 29 pull for bi-directional motion with a significant mechanical advantage. The tilt mechanism is similar and therefore the tilt motor and capstan are not shown.

The counterweight 43 can be adjusted so as to have the robot center of mass as close as possible to the intersecting revolute arm axes 24 and 26 but below UP-DOWN capstan drive asix 24. The robot structure that moves around axis 24 has center of mass below horizontal axis 24. This means that when the motors are deactivated, the robot remains in its position or returns to a neutral counterbalanced position and does not "fall down".

Passive/Active Hand Controller 2

A number of commercially available devices can be used as passive six-axis controllers or joysticks 2. In particular, a SpaceMouse device developed by Space Systems Inc and distributed by Logitech as the Magellan device can be used to sense the operator's hand motions. A force-torque sensor can be used to sense the operator's hand forces.

A haptic interface as reported in (Hollis et al., U.S. Pat. No. 5,146,566) can be used as an operator hand interface 2. This type of interface not only detects displacements or forces, but can also exert motions or forces on the user's hand by means of at least one actuator.

The use of several hand controllers with fewer degrees of freedom can also be employed. For example, two three-degree-of-freedom hand-controllers/joysticks can be used instead of a six-degree-of-freedom hand-controller/joystick. One hand controller can control the probe translational position, while the other can control the probe orientation. Similarly one active hand controller/haptic interface can display the ultrasound probe forces while the other hand controller/haptic interface can display the ultrasound probe torques.

Controller 3

The robotically-assisted medical ultrasound examination system comprises a controller 3, having input-output cards and a computer/microprocessor. If needed for faster processing an additional image processing computer 5 can be used that is connected to the controller 3 by standard data transfer connections such as serial, parallel or data bus.

The input-output cards comprise means to measure the robot motor angles from motor 31–36 (sensing electronics 61 in FIG. 2) encoders and means to activate the robot motors M1–M6. For example optical encoders and decoder electronics, and digital-to-analogue converters followed by voltage-controlled current output power amplifiers can be used.

The input-output cards also comprise means to read and specify the positions or velocities and the forces of the hand controller 2 (these depend on the particular hand-controller hardware but have been documented before) via sensing electronics 60.

In addition, the controller 3 or the image processing computer 5 has input cards that allow the ultrasound image produced by the ultrasound machine to be acquired as a two-dimensional array of pixel values. For example, a frame-grabber can be used to acquire ultrasound images from the ultrasound machine video-out connection that is used to record videotapes of examinations.

Ultrasound Machine 4

The ultrasound machine 4 can be an off-the-shelf standard machine that provides a video output of the ultrasound image on a display monitor 52. This image can be digitized and put in the memory of the system controller 3 or the memory of an image processing computer 5 by a standard frame grabber board such a Matrox Meteor. The machine can also provide direct digitized images to the system controller 3 or to the image processing computer 5.

Software Interfaces

Software modules developed according to known art allow a standard software interface to the ultrasound probe positioning robot 1 such that:

A programmer can obtain the values of the ultrasound probe 6 position Pr (or velocity Vr) and forces Fr exerted by the environment on the ultrasound probe 6 in all six degrees of freedom—three translations and three orientations with respect to a fixed frame of reference;

A programmer can set commanded or desired ultrasound probe 6 position Pr0 (or velocity Vr0) and forces Fr0 exerted by the environment on the ultrasound probe 6 in all six degrees of freedom (a linear combination of positions or velocities with forces is also possible), which are then transformed to motor currents according to known dynamics and control algorithms.

Software modules developed according to known art also allow a standard software interface to the hand controller hardware 2 such that:

A programmer can obtain the values of the hand controller 2 position Ph (or velocity Vh) and forces Fh the hand controller exerts on the hand of the operators 50 in all six degrees of freedom;

A programmer can set commanded or desired hand-controller 2 position Ph0 (or velocity Vh0) and desired hand-controller forces Fh0 (a linear combination of positions or velocities with forces is also possible).

Figure 3:
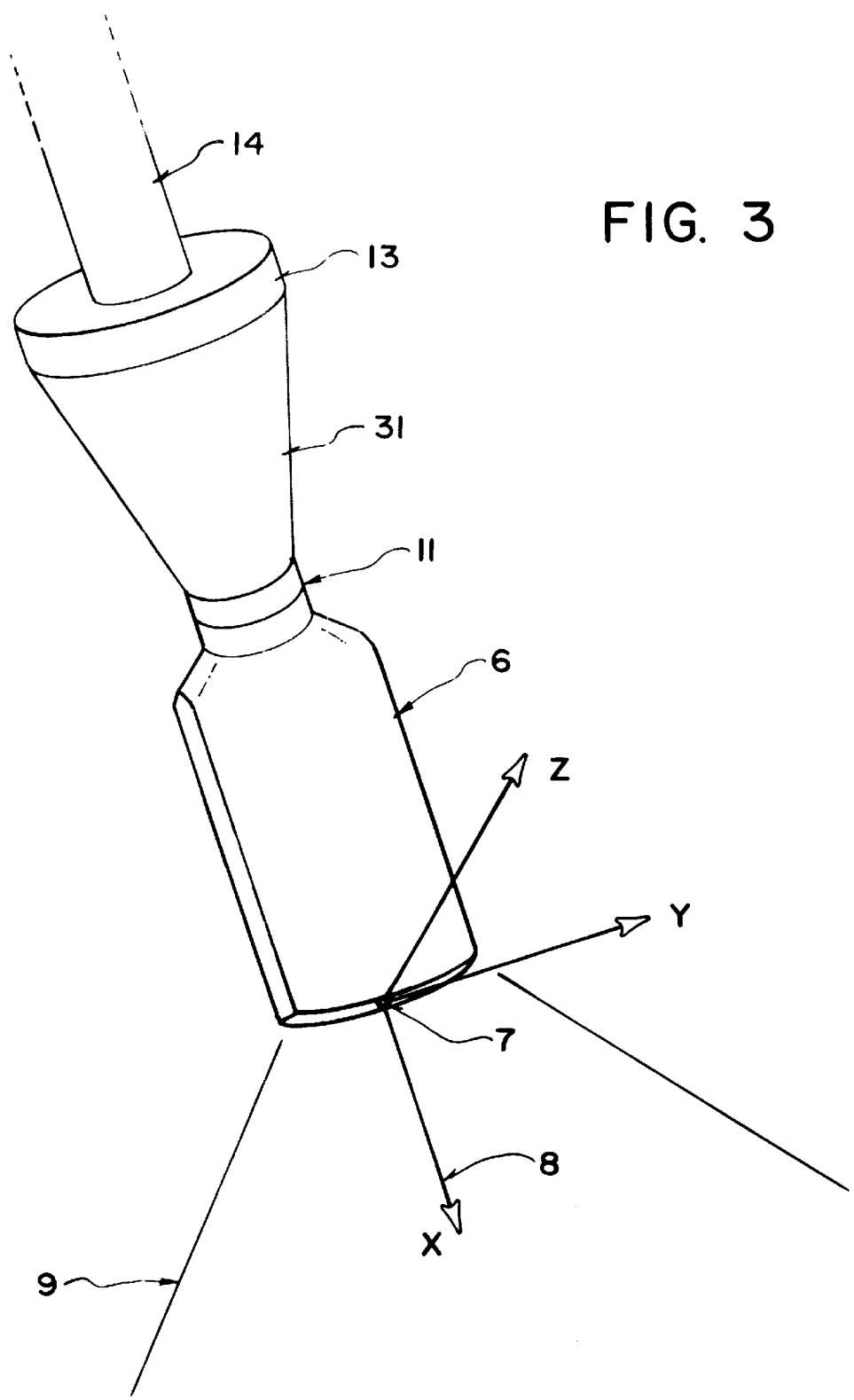
FIG. 3 illustrates a detail enlarged isometric view of the ultrasound transducer with coordinate system and imaging plane.

It is understood in the above that "positions" means positions and orientations, and "forces" means forces and torques. As illustrated in FIG. 3, the reference point 7 on the ultrasound probe when its position is specified is the ultrasound probe tip that generates the ultrasound imaging plane 9 and that is normally in contact with the patient. A similar interface for the use of two or more hand controllers, instead of a single hand controller, can be formulated in a similar manner and should be obvious to those skilled in the art.

Software modules developed according to known art allow a standard software interface to the ultrasound machine hardware 4 such that:

A programmer can obtain the ultrasound images as a two-dimensional array of intensities g(x,y,Pr) that is a function of the ultrasound probe 2 position and orientation Pr and it specifies pixel values along ultrasound probe planar beam co-ordinates x and y, as shown in FIG. 3. The probe planar beam in FIG. 3 impinges along the probe x-axis 8 that lies in the ultrasound image plane 9 containing the x and y vectors of the co-ordinate system 7 attached to the ultrasound probe tip 6. Polar co-ordinates in the ultrasound beam plane could also be used.

A programmer can obtain the motion estimate (dx,dy) of a subset of the ultrasound image g1(x,y,Pr) from one acquired ultrasound image g(x,y,Pr,t) at time t to another acquired ultrasound image g(x,y,Pr,t+dt) at time t+dt.

To obtain such motion estimate, (dx,dy) over the time interval dt, known algorithms based on pixel value correlation, phase correlation or feature tracking could be used.

A programmer can obtain an estimate of the signal to noise ratio in the ultrasound image g(x,y,Pr,t). A programmer can also obtain an estimate of the specularity in the ultrasound image g(x,y,Pr,t).

Figure 4:
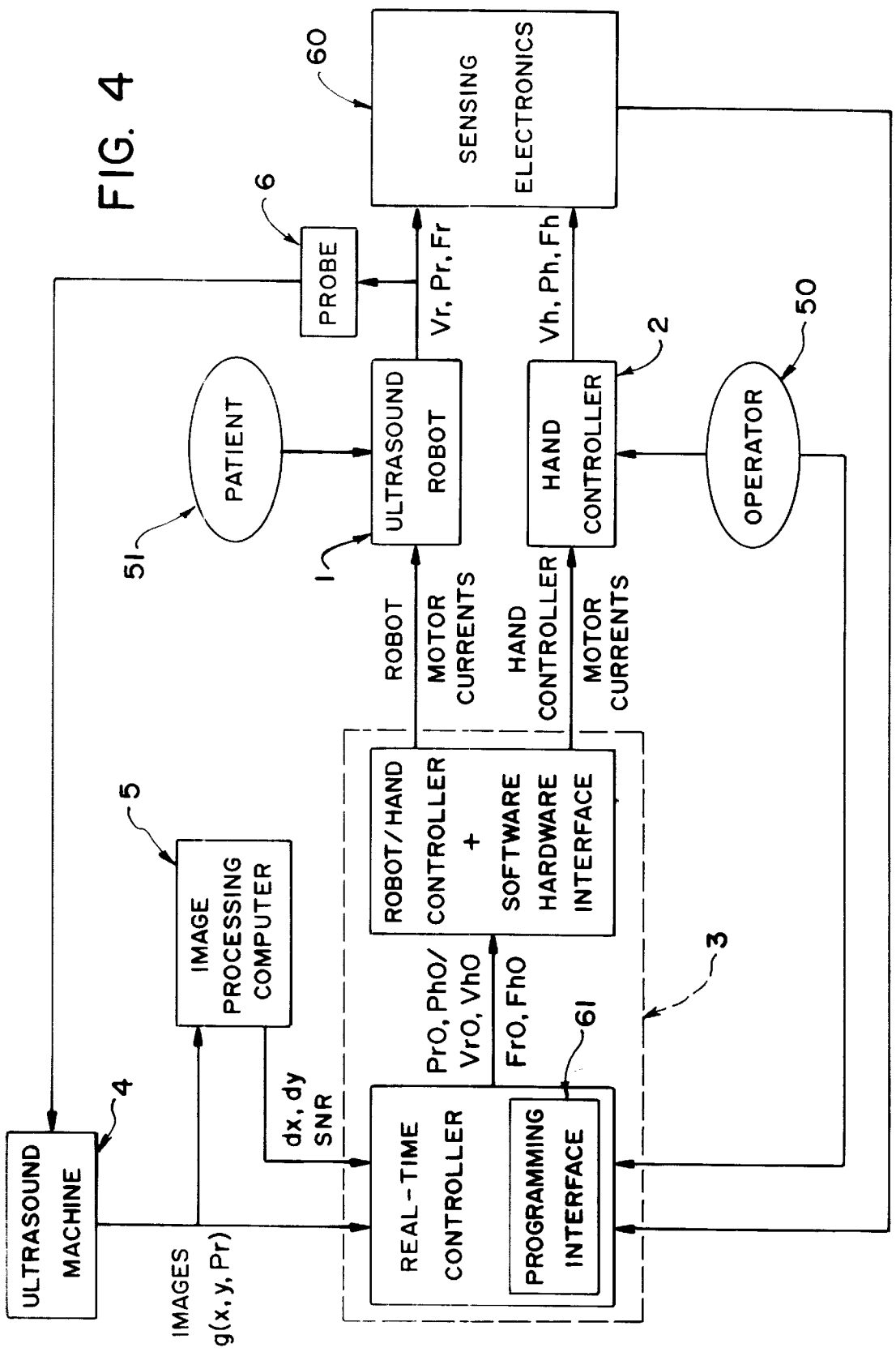
FIG. 4 illustrates a schematic of the method of using the robotically assisted medical ultrasound.

It is proposed that the robotically assisted medical ultrasound examination system proposed in this invention, with physical components shown in FIG. 1 and summarized functionally in FIG. 4, be used in the following novel ways:

Operator Control.

The operator 50 controls the system in a master-slave mode, with the operator hand manipulating the hand-controller 2. The ultrasound probe will track operator positions, velocity or force commands, by appropriate setting of the command signals in the programming interface 61. If one (the programmer or the operator via the user interface 61) sets Vr0=Vh, Pr0=Ph, the ultrasound probe 6 tracks the position of the hand-controller, if one sets Vr0=Ph the ultrasound probe velocity tracks the hand-controller position (measured from the nominal centre of the hand controller 2), and if one sets Fr0=Fh, the ultrasound probe force will track the hand-controller force. Such assignment can be done component-wise, with some axes being controlled in force-tracking mode, while others being controlled in position or velocity tracking mode. Since the ultrasound probe cannot track hand-controller velocities and forces along the same axis, the ultrasound force level Fr can be compared against a threshold value. Whenever Fr exceeds a threshold value Frmin, the ultrasound probe can be controlled in force mode, by setting Fr0=Fh. Otherwise, the probe is controlled in velocity mode. Alternatively, a "virtual decomposition" approach (Zhu et al., 1998) can be used that ensures that the linear combination Vr+K Fr of the ultrasound probe closely follows a set point which can be set to the hand displacement Ph where K is a scaling matrix that can be diagonal. The ultrasound probe velocity Vr will follow the hand controller position Ph if the ultrasound probe is unconstrained (Fr will be zero in this case) and causes the ultrasound probe force Fr to follow the hand controller force Fh if the ultrasound probe is pushing against a soft or hard constraint (Vr is approximately zero in this case as the probe pushes on the patient). If the hand controller 2 is active and can provide force-feedback to the user, one can set Fh0=Fr in the programming interface. Thus, with an active hand controller 2, the hand controller force Fh closely follows the force Fr the environment exerts on the ultrasound probe 2, allowing a more direct and intuitive control of ultrasound probe forces. It is clear in the above discussion that scaling factors can be used in setting the command values, for example Pr0=scaling_factor * Ph achieves a motion of the ultrasound probe that is scaled (in all directions) by a six-by-six scaling matrix scaling_factor that can be selected by the programmer of the robot-assisted ultrasound diagnostic system or can be selected by users for their comfort. It is also clear to the skilled in the art person that the probe velocity and force command value of the ultrasound probe can be specified in a co-ordinate system 7 attached to the ultrasound probe (as shown in FIG. 3). For example, if R_Vr and R_Vr0 denote the ultrasound probe velocity and its command value, respectively, expressed in the ultrasound probe co-ordinate system 7, setting R_Vr0= Ph commands the ultrasound probe velocity so that the translational and rotational components of Vr track the translational and rotational components of the hand position Ph rotated from the hand controller frame into the ultrasound probe frame. This is equivalent to applying a rotation transformation to Ph before assigning the value to Vr0, or Vr0=Q * Ph, where Q is a rotation transformation matrix such that Q*Ph is the vector Ph expressed in the ultrasound probe frame.

Shared Control.

In such a mode, the operator 50 controls the motion of the ultrasound probe 6 along some degrees of freedom, as described in the Operator control section above, while the computer 3 controls the motion along others, hence the term "shared control". For example, in a particular implementation, the operator can lock the translational motion of the ultrasound probe 6 at its current location Pr_lock_translation, by using a keyboard, switch or other means included in the programming interface 61 to set Pr0_translation=Pr_lock_translation, in the controller software. The index_translation denotes the translational component of a six-parameter position/orientation or force/torque vector. The operator 50 continues to control the orientation of the ultrasound probe about its tip by using the hand controller 2, by setting the ultrasound probe orientation to that of the hand controller, i.e. Pr0_rotation=Ph_rotation, or alternatively, by setting the ultrasound probe angular velocity to the hand orientation, Vr0_rotation=Ph_rotation, for the ultrasound probe 6 rotational velocity to follow the hand controller 2 orientation. The index rotation denotes the rotational component of a six-parameter position/orientation or force/torque vector. Again, scaling factors can be used in the above, for example Vr0_rotation= scaling_factor * Ph_rotation, so that scaled values of hand displacements are used to determine the ultrasound probe velocity.

In another example of shared computer/user control of the ultrasound probe, command signals in the programming interface 61 could be set by the operator so that the robot applies a fixed force along the axis 8 (see FIG. 3) of the ultrasound probe 6, while the operator controls the probe position in a plane orthogonal to the ultrasound plane axis, as well as the probe orientation. This is achieved by setting in the programming software interface Fr0_probe_axis= Fr0_desired, where Fr0_probe_axis is the command force along the ultrasound probe axis (8 in FIG. 3), while the other motion axes are controlled as described in the Operator control section above. Again, scaling factors or appropriate rotation matrices can be used in the above shared control method.

In another example of shared control of the ultrasound probe 6, the ultrasound probe orientation can be fixed to a set value, while its translational components are controlled by the ultrasound machine operator 50 via the hand controller 2. This keeps the probe in a constant orientation and allows the operator to translate the probe for fine motions with greater ease.

Taught Control.

The computer can remember trajectories (positions and forces), thereby allowing effortless repeat scans of the neighbouring parts of the human body 51. This can be achieved by an operator-activated recorder that keeps track of the ultrasound probe trajectory Pr(t) for a time t interval between t0 and t1 seconds. When the operator wishes to repeat the motion T seconds later, a switch or keyboard or equivalent command can be given to the real-time controller that will command the robot controller to repeat the trajectory by setting Pr0(t)=Pr(t−T), in effect playing back the motion that took place T seconds ago. It is clear that the recording of trajectories can be done for all or only for certain components of Pr, for all or only for certain ultrasound probe velocity components Vr, for all or only for certain components of the ultrasound force components Fr, or combinations of these Pr, Vr and Fr components.

Ultrasound Image Tracking Mode.

There may be instances in which ultrasound image features need to be recognized and tracked. In the following example, we describe how such features can be tracked by computer automatically. Suppose, for example, that a blood vessel such as the carotid artery needs to be scanned longitudinally. The operator can find and mark a region of interest (gl(x,y,Pr)) on the ultrasound machine display screen 52 (see FIG. 1). This region of interest is recorded by the image processing computer 5 (see FIGS. 1 and 4) that can generate its displacement co-ordinates dx and dy within the image displayed. For such displacement estimation, a number of schemes have been proposed and demonstrated to work, including image correlation, image phase correlation, and feature extraction and tracking. The displacement co-ordinates dx and dy can then be transformed by the real-time controller (see FIG. 4) into an equivalent ultrasound robot co-ordinates displacement dPr by using well known kinematic and Jacobian transformations. The robot controller then applies, at all times, a corrected robot trajectory Pr0=Pr0−dPr, that results in the robot moving the ultrasound probe so that the region of interest to the operator is kept in the center of the displayed ultrasound image. The above correction can be applied to directions that are in the plane of the ultrasound imaging beam, while the operator continues to control the robot motion by hand-controller commands along other axes. Alternatively, the above correction can be added to the command Pr0 generated from the hand controller (for example, Pr0=Ph−dPr, or alternatively, for velocity control,. Vr0=Ph−dPr/dt, where dt is the time interval between motion estimates). This type "visual servoing" results in the ultrasound probe maintaining the region of interest in the field of view displayed to the operator on monitor 52 for reasonably long periods of time, and even if the image features change considerably. Visual servoing has been implemented before with conventional videocamera images but not with ultrasound images. Note that, in particular, the image "feature" tracked could be a needle that is being inserted during an intervention.

3-D Reconstruction Mode.

Many of the 3-D ultrasound systems reported use an ultrasound probe position sensor to register planar scans and perform three-dimensional reconstructions based on these planar scans. One of the advantages of the proposed robotically assisted ultrasound examination system is that the robot sensors can be used for image registration for 3-D ultrasound. In one method of operation of the proposed invention, the robot carrying the ultrasound probe can be programmed by means of the system controller 3 to acquire several ultrasound scans at different motion increments of the ultrasound transducer 6, where the motion increments are essentially lateral to the scanning plane 9. The acquired images can be registered against a fixed reference and a three-dimensional image can be created. For example, assume that the ultrasound probe is positioned so that the beam axis 8 is essentially orthogonal to a part of the patient's 51 anatomy. A series of incremental translations of the ultrasound probe 6 along a direction orthogonal to the ultrasound probe beam plane 9 (this is direction z in FIG. 3) can be programmed, with the ultrasound machine acquiring a series of planar ultrasound images after each motion increment. The series of planar ultrasound images can then be registered and merged in a volumetric three-dimensional image according to known art (eg. Fenster, 1998).

The ability to have controlled motion of the ultrasound probe allows for improved Signal-to-Noise Ratio (SNR) in 3-D ultrasound by using a SNR monitoring system, also implemented on the image processing computer 5 using known estimation and identification methods. During imaging acquisition, if the SNR value drops under a given threshold, the real-time controller can automatically repeat the scanning motion and generate better images through averaging. For example, if the scanned image g(x,y,Pr,t) is poor when the ultrasound transducer 6 is positioned at the point Pr=Pr1, the robot controller can re-program the scanning trajectory so Pr(t)=Pr1 at a number of time instances t1, t2, t3, etc. Averaging of images g(x,y,Pr,t1), g(x,y,Pr,t2), etc. can improve the resulting 3-D ultrasound image.

In addition, the volume that has to be swept for a 3-D ultrasound image can also be scanned by the ultrasound robot in a manner the optimizes the SNR. For example, the same body volume can be scanned by using different ultrasound probe yaw angles. The ultrasound robot can repeat scans at different angles, selecting the angles with the highest SNR for repeated scans. It is also possible to automatically add an orientation or position increment deltaPr(t) to the desired trajectory Pr0(t) for a 3-D scan such that the increment deltaPr(t) minimizes the SNR at Pr0(t). Such an increment deltaPr(t) can be obtained by small perturbation of the probe position and orientation about Pr(t) while monitoring the SNR. The perturbation with an increase in the SNR can be added to the pre-planned 3-D scanning trajectory.

In the above description, it should be noted that the signal to noise ratio in ultrasound images may be only one factor of image quality that is being considered. Other measures that embody ultrasound beam reflections or image specularity can be considered in a similar manner.

In addition, the proposed robot-assisted ultrasound system could also be used to acquire three-dimensional ultrasound images by scanning the same body volume from different ultrasound probe trajectories, in effect using different "views" to acquire an image of the same anatomical volume. Different views generate images with different reflection patterns and therefore averaging the images obtained for the same volume from different views improves the three-dimensional image of the volume of interest.

Direct Robot Teaching Mode.

Another mode of operation would be for the operator to hold the ultrasound probe 2 while the probe is attached to the ultrasound robot 1, instead of manipulating the hand controller 2. As the forces applied to the ultrasound probe by the operator's hand are sensed, these forces can be used to generate motion of the ultrasound probe 6 along or about permissible axes, with the manipulator restricting or resisting motion along or about non-permissible axes. The manipulator could also limit the workspace or the force levels in certain or all directions.

Mixed Modes.

The above control modes of operation can be mixed so that shared control along one or several axes can be used with taught control along one or several control axes and with ultrasound tracking mode along one or several axes, and even with 3-D reconstruction mode. For example, for the carotid artery examination, the operator may control the movement of the probe along the longitudinal axis of the carotid artery, while the real-time controller controls the motion of the probe orthogonal to the carotid artery, and the probe orientation is controlled by computer to a fixed value (image axis crossing the neck) or modified by small perturbations to obtain a good signal to noise ratio. The commanded trajectories Pr0/Vr0 or Fr0 to the ultrasound robot can be obtained by adding weighted sums of command trajectories generated from the above modes, in particular these weighted sums allowing for the selection of co-ordinate axes, different scaling values or rotations so that the commands are given relative to different reference frames.

Benefits of the Invention

Ultrasound as a medical imaging modality has a number of benefits—it is inexpensive, non-invasive, real-time, etc. It is used widely for diagnosis, and also in interventions, for example, to guide needles or other instruments for anaesthesis and surgery. The present invention, while adding substantial cost to an ultrasound system, has a number of advantages.

Ergonomic Ultrasound Interface.

Instead of manipulating the ultrasound transducer by hand, ultrasound technicians can manipulate a hand controller or a probe that can be ergonomically designed. Medical ultrasound exams usually require an ultrasound technician to hold the transducer probe with one hand while adjusting scanning parameters with the other. Often, the ultrasound technician is required to stand in awkward positions or exert large forces for prolonged periods of time. Not surprisingly, a number of recent studies indicate that ultrasound technicians suffer from an unusually high incidence of musculoskeletal problems.

Tele-Radiology.

Methods have been presented in the literature for transmitting ultrasound images for tele-radiology applications. The subject invention augments these methods by allowing the radiologist to not only view remote ultrasound images, but also to manipulate the ultrasound transducer at the remote site.

Smart 3-D Ultrasound.

Since the position and orientation of the ultrasound transducer can be determined using the forward kinematics of the slave manipulator, the invention can be used to generate three-dimensional ultrasound images in an optimal way. Currently, 3-D ultrasound images are generated by passive tracking of the ultrasound probe and computer reconstruction. With a computer-controlled probe, the computer reconstruction can use current images to plan the ultrasound probe trajectory. Both the motion of the probe and the image processing algorithm can be adjusted to improve the reconstruction.

Image-Guided Surgery and Anaesthesia.

The subject system can also be used intra-operatively or for anaesthesis in order to guide the surgeon or anaesthetist in the positioning of needles or instruments inside the human body. Once a 3-D image is acquired, it can be used to register the position of organs with respect to pre-operative images. One example of use would be in the ROBODOC system, in which the femur position must be registered with respect to CT scans for precise robot-based milling of the implant hole in the bone.

As will be apparent to those skilled in the art in the light of the foregoing disclosure, many alterations and modifications are possible in the practice of this invention without departing from the spirit or scope thereof. Accordingly, the scope of the invention is to be construed in accordance with the substance defined by the following claims.

REFERENCES

| U.S. Patents: | | |
| --- | --- | --- |
| U.S. Pat. No. | Issue Date | Inventor |
| 5,538,004 | Jul. 23, 1996 | Bamber |
| 5,572,999 | Nov. 12, 1996 | Funda et al. |
| 5,485,846 | Jan. 23, 1996 | Webler et al. |
| 5,482,043 | Jan. 9, 1996 | Zulauf |
| 5,413,106 | May 9, 1995 | Fujita et al. |
| 5,396,890 | Mar. 14, 1995 | Weng |
| 5,315,512 | May 24, 1994 | Roth |
| 5,291,401 | Mar. 1, 1994 | Robinson |
| 5,551,432 | Sept., 1996 | Iezzi et al. |
| 5,842,993 | Dec., 1998 | Eichelberger et al. |
| 5,836,880 | Nov., 1998 | Pratt |
| 5,810,008 | Sept., 1998 | Dekel et al. |
| 5,759,153 | June, 1998 | Webler et al. |
| 5,853,367 | Dec., 1998 | Chalck et al. |
| 5,797,849 | Aug., 1998 | Vesely et al. |
| 5,817,022 | Oct., 1998 | Vesely et al. |
| 5,842,473 | Dec., 1998 | Fenster et al. |
| 5,562,095 | Oct., 1996 | Downey et al. |
| European Patent: | | |
| Patent No. | Date | Inventor |
| 0 514 584 A2 | Nov., 1992 | Solomon et al. |
| Canadian Patents: | | |
| Patent No. | Issue Date | Inventor |
| 2,166,579 | Nov. 27, 1996 | Seiji et al. |

Publications:

M. Craig, "Sonography: An occupational health hazard?" *Journal of Diagnostic Medical Sonography*, vol. 1, pp. 121–124, May/June 1985.

H. E. Vanderpool, E. A. Friis, B. S. Smith, and K. L. Harms, "Prevalence of carpal tunnel syndrome and other work-related musculoskeletal problems in cardiac sonographers", *Journal of Occupational Medicine*, vol. 35, pp. 604–610, June 1993.

J. F. Brinkley, W. E. Moritz, and D. W. Baker. Ultrasonic three-dimensional imaging and volume from a series of arbitrary sector scans. *Ultrasound in Medicine and Biology*, 4:317–327, 1978.

J. W. Sublett, B. J. Dempsey, and A. C. Weaver. Design and implementation of a digital teleultrasound system for real-time remote diagnosis. In *Proceedings of the 1995 Sympo-sium on Computer-Based Medical Systems*, pages 292–298, 1995.

B. G. Barnett, J. J. Bloomer, R. L. S. Peters, and E. T. Saulnier, "A modular framework for teleradiology", in *Medical Imaging* 1993. *PACS Design and Evaluation*, pp. 376–382, 1993.

W. J. Chimiak, N. T. Wolfman, and J. M. Boehme, "Results of a clinical test of an ATM tele-ultrasound system", in *Medical Imaging* 1996. *PACS Design and Evaluation, pp.* 180–184, 1996.

E. Cordonnier, M. Eichelberg, J. Piqueras, C. Treguier, and J. F. Heautot, "European project Retain: New approach for IBC in teleradiology and PACS based on a full ATM network", in *Proceedings of the IEEE International Conference on Image Processing*, pp. 1–4, 1996.

A. J. Duerinckx, A. Hayrapetian, E. G. Grant, D. J. Valentino, D. Rahbar, and M. Kiszonas, "Impact of ultrasound video transfer on the practice of ultrasound", in *Medical Imaging* 1996: *PACS Design and Evaluation, pp.* 168–179, 1996.

S. J. Dwyer, A. W. Templeton, W. H. Anderson, K. S. Hensley, M. A. McFadden, B. K. Stewart, J. C. Honeyman, L. T. Cook, K. G. Baxter, R. Y. Wingard, and C. L. Hall, "Teleradiology using switched dialup networks", *IEEE Journal on Selected Areas in Communications*, vol. 10, pp. 1161–1172, September 1992.

A. Fenster and D. B. Downey, "3-D ultrasound imaging: A review", *IEEE Engineering in Medicine and Biology*, pp. 41–51, November/December 1996.

S. L. Fritz, S. R. Roys, W. T. DeJarnette, D. Csipo, and J. Conners, "An ACR-NEMA 2.0 based teleradiology system", in *Medical Imaging* 1993: *PACSDesign and Evaluation*, pp. 332–338, 1993.

R. W. Martin, G. Bashein, R. Zimmer, and J. Sutherland, "An endoscopic micromanipulator for multiplanar transesophageal imaging", *Ultrasound in Medicine and Biology*, vol. 12, no. 12, pp. 965–975, 1986.

R. Martinez, S. Robles, and J. Kim, "PC-based workstations for global PACS remote consultation and diagnosis in rural clinics", in *Medical Imaging* 1995: *PACS Design and Evaluation*, pp. 220–231, 1995.

P. H. Mills and H. Fuchs, "3D ultrasound display using optical tracking", in *Visualization in Biomedical Computing*, pp. 490–497, 1990.

R. Ohbuchi and H. Fuchs, "Incremental 3D ultrasound imaging from a 2D scanner", in *Visualization in Biomedical Computing*, pp. 360–367, 1990.

T. Paakkala, J. Aalto, V. Karara, and S. Seppanen, "Diagnostic performance of a teleradiology system in primary health care", *Computer Methods and Programs in Biomedicine*, vol. 36, pp. 155–160, 1991.

B. K. Stewart, S. J. Carter, J. Cook, B. S. Abbe, D. Pinck, and A. H. Roubergs, "Real-time compressed video ultrasound using the advanced communications technology satellite", in *Medical Imaging* 1996: *PACS Design and Evaluation*}, pp. 194–204, 1996.

W. H. Zhu, et al., "Virtual decomposition approach for the control of complex robotic system", IEEE International Conference on Robotics and Automation, Leuven, Belgium, 1998.

What is claimed is:

1. A method of positioning an ultrasound transducer onto the surface of a human body comprising: mechanically positioning the ultrasound transducer on the surface of the human body by an operator positioned remotely from the ultrasound transducer operating a hand controller which is linked to the ultrasound transducer and which by means of a programmed computer instructs and causes the ultrasound transducer to be positioned on the surface on the human body, the ultrasound transducer acquiring and transmitting ultrasound images to a display viewed by the operator, said computer being programmed to prevent an above threshold level normal force being exerted on the human body.

2. A method as claimed in claim 1 wherein the hand controller controls electronically and remotely the position of the ultrasound transducer on the human body.

3. A method as claimed in claim 1 wherein the hand controller controls electronically and remotely the velocity of the ultrasound transducer over the human body.

4. A method as claimed in claim 1 wherein the hand controller controls electronically and remotely the force exerted by the ultrasound transducer on the human body.

5. A method as claimed in claim 1 wherein the hand controller controls electronically and remotely a combination of velocity and force of the ultrasound transducer on the human body.

6. A method as claimed in claim 1 wherein the hand controller controls only some of the degrees of freedom available to the ultrasound transducer and a control computer controls the others.

7. A method as claimed in claim 1 wherein the computer is programmed to hold the ultrasound transducer at a fixed position on the human body, and the operator controls the orientation of the ultrasound transducer.

8. A method as claimed in claim 1 wherein the force exerted by the transducer is controlled by the computer according to a force sensor reading and the operator is permitted to control orientation of the ultrasound transducer.

9. A method as claimed in claim 1 wherein normal force exerted by the transducer is controlled by the computer but the orientation of the ultrasound transducer is adjusted to a stated program value in the computer.

10. A method as claimed in claim 1 wherein the connection between the positioning of the ultrasound transducer and the operator and the hand controller is performed by means of a counterbalanced robot.

11. A method as claimed in claim 10 wherein the program in the computer controls certain degrees of freedom and the counterbalanced robot controls other degrees of freedom.

12. A method of performing an ultrasound examination on a person comprising using a robot arm to position an ultrasound probe on the surface of the person according to shared control of a remotely positioned ultrasound operator and a programmed computer, the ultrasound probe acquiring and transmitting ultrasound images in real time to a display viewed by the operator, said shared control incorporating a method to prevent an above threshold level force being exerted on the person.

13. A method according to claim 12 wherein the ultrasound transducer probe information is displayed on the monitor, and the operator activates the hand controller to regulate the force applied by the ultrasound transducer probe on the surface of the human body.

14. A method as claimed in claim 12 wherein the operator controls motion of the ultrasound transducer probe along certain degrees of freedom and the programmed computer controls the motion of the ultrasound transducer probe along other degrees of freedom.

15. A method as claimed in claim 12 wherein the computer is programmed to recall trajectories followed by the ultrasound transducer probe during a prior ultrasound scan of the human body.

16. A method as claimed in claim 12 wherein the computer is programmed to recall serial positions and serial forces applied by the ultrasound transducer probe during a prior serial position and serial force trajectory followed by the ultrasound transducer probe on the human body.

17. A method as claimed in claim 12 wherein the computer is programmed to repeat scans of the ultrasound transducer probe from different incremental positions on the human body lateral to the scan direction and rationalizes the repeated scans to generate a three-dimensional ultrasound image on the monitor.

18. A method according to claim 12 wherein the computer is programmed to perform mixed modes of operation wherein the operator shares control of the position of the ultrasound transducer probe along certain axes with taught control programmed into the computer and a tracking mode along a plane is programmed in the computer while the operator controls the movement of the ultrasound transducer probe along the remaining degrees of freedom.

19. A method according to claim 12 wherein control of the position, force or velocity of the ultrasound transducer is shared between the operator and the computer and determined according to the ultrasound image.

20. A method as claimed in claim 12 wherein the operator uses an input device to input a component of motion control to the transducer to scan new parts of the human body and to input a component of orientation control to the transducer while observing the ultrasound images generated by the ultrasound image monitor to maximize image signal-to-noise ratio.

21. A method as claimed in claim 12 wherein ultrasound image features are processed by the computer to determine the optimum orientation of the transducer and provide an automatic orientation control signal component which is added to the attitude control input from the operator's input device.

22. A method as claimed in claim 12 wherein the transducer image features are processed by the computer to provide an automatic direction control signal component which tracks relevant anatomical structures under the surface of the skin of the human body.

23. A method as claimed in claim 12 wherein the computer senses the force vector applied by the operator to the input device and scales said force up or down and adds it to a predetermined force applied between the transducer and the human body.

24. A method as claimed in claim 12 wherein the input device is capable of displaying a force vector to the operator that is computed by the computer based scaling the actual force observed at the probe/skin interface of the human body.

25. A method as claimed in claim 12 wherein the direction of motion of the transducer is determined from a recording of a previous scan.

26. A method as claimed in claim 12 wherein the hand controller is a joy stick which provides force feedback to the operator.

27. An apparatus for positioning an ultrasound transducer onto a human body comprising:
(a) a mechanism to position the ultrasound transducer on the human body;
(b) a hand controller to enable an operator to input into a computer a desired position, a desired velocity or a desired force, or a linear combination thereof; and
(c) a computer control that maps the operator input into the ultrasound transducer position, velocity or force, said computer being programmed to prevent an above threshold level normal force being exerted by the ultrasound transducer on the human body.

28. An apparatus as claimed in claim 27 wherein the hand controller controls the position of the transducer.

29. An apparatus as claimed in claim 27 wherein the hand controller controls the velocity of the transducer.

30. An apparatus as claimed in claim 27 wherein the hand controller controls the force of the transducer.

31. An apparatus as claimed in claim 27 wherein the hand controller controls a linear combination of velocity and force of the transducer.

32. An apparatus as claimed in claim 27 wherein the hand controller is a 6 degrees of freedom joy stick which provides force-feedback to an operator of the apparatus.

33. An apparatus as claimed in claim 32 wherein the joy stick controls only some of the degrees of freedom of the transducer.

34. An apparatus as claimed in claim 27 wherein the mechanism is a counterbalanced robot.

35. An apparatus as claimed in claim 34 wherein the robot has a 4-bar parallelogram linkage wrist.

36. An apparatus as claimed in claim 27 including a 6 degrees of freedom rate control device.

37. An apparatus for performing ultrasound on a person comprising:
(a) a 4-bar parallelogram linkage wrist robot arm with an ultrasound transducer for positioning the transducer on the surface of the body of the person;
(b) a passive or active hand controller which is operated by an operator to instruct the robot arm to position the ultrasound transducer on the surface of the body of the person; and
(c) a computer which is programmed to coordinate motion and force of the robot and hand controller as a function of operator input, sensed parameters and ultrasound images.

38. An apparatus as claimed in claim 37 wherein the operator controls the apparatus in a master-slave mode, and the robot tracks operator position, velocity or force.

39. An apparatus as claimed in claim 37 wherein the hand controller is passive.

40. An apparatus as claimed in claim 37 wherein the hand controller is active.

41. An apparatus as claimed in claim 27 wherein said computer control is programmed to enable free motion of the ultrasound transducer in relation to position and velocity but restricting force of the ultrasound transducer along directions constrained by the human body.

42. An apparatus as claimed in claim 27 wherein the apparatus includes a mechanism that breaks away when a normal force above a prescribed limit is exerted on the human body.

43. An apparatus as claimed in claim 37 including a monitor, wherein ultrasound transducer probe information is displayed on the monitor in real time, and the operator activates the hand controller to regulate the normal force applied by the ultrasound transducer probe on the surface of the human body.

* * * * *